United States Patent [19]

Hess

[11] 4,225,587

[45] Sep. 30, 1980

[54] METHOD OF REPELLING INSECTS BY SYSTEMIC ACTION IN HUMANS ON SULFUR AND SULFUR CONTAINING SUBSTANCES

[76] Inventor: Laurie F. Hess, c/o Resources Engineering Inc., 2025 Eye St. NW., Suite 506, Washington, D.C. 20006

[21] Appl. No.: 857,501

[22] Filed: Dec. 5, 1977

[51] Int. Cl.³ ...................... A01N 59/02; A61K 33/04
[52] U.S. Cl. .................................... 424/162; 424/125; 424/164; 424/317; 424/DIG. 8; 424/DIG. 10
[58] Field of Search ................ 424/125, 162, DIG. 10

[56] References Cited

PUBLICATIONS

Merck Index, 7th Ed. (1960), p. 1004.
Chemical Abstracts, vol. 60 (1964), p. 8543d.
Chemical Abstracts, vol. 49 (1955), p. 1190f.
Welcome, "Excerpta Therapeutica", p. 165.

*Primary Examiner*—Leonard Schenkman
*Attorney, Agent, or Firm*—Frank L. Abbott

[57] ABSTRACT

The disclosure relates to a method of repelling insects from humans, with sulfur as an element or combined or mixed with other substances, by the systemic action in the human body; and also the substances produced by the systemic action on the exposed surfaces of the body such as the skin or membranes.

16 Claims, No Drawings

METHOD OF REPELLING INSECTS BY SYSTEMIC ACTION IN HUMANS ON SULFUR AND SULFUR CONTAINING SUBSTANCES

OBJECT OF THE INVENTION

An object of the invention is to create a human body condition which is repellent to insects by introducing sulfur or sulfur combined or mixed with other substances into the body.

Another object is to provide humans with prolonged protection from insects by administering dosages of sulfur or sulfur combined or mixed with other substances.

Another object is to create a skin condition in humans which is repugnant to biting or sucking insects such as chiggers, mosquitoes, flies, etc. by ingesting sulfur or sulfur combined or mixed with other substances.

Another object is to create a mucous membrane condition that is repugnant to biting, sucking or chewing insects.

Another object is to create the repugnant condition in either the skin or mucous membrances by introducing the sulfur or sulfur combined or mixed with other substances into the body by using a rectal suppository or by injecting the condition-creating substance directly into the tissues.

There has been a long-felt need for a systemic insect repellent by many people such as hunters, fishermen, the military and agricultural and construction workers who spend prolonged periods in an outdoors environment infested with biting, sucking, or chewing insects. Heretofore, the common available relief was in the form of pesticides which could be painted or dusted upon the exposed body portions.

Systemic insecticides are not unknown and have been used in plants, for example: U.S. Pat. No. 3,793,452 discloses the systemic application of a compound or mixture of compounds which, when applied to the roots of growing plants, are translocated through the plants to render the plants toxic to sucking or chewing insects.

It is comtemplated by this specification and claims that, through the intake of sulfur, sulfur mixture or sulfur compounds into the body orally, by suppository or by injection into the tissues, the component of perspiration or saliva containing sulfur is increased to a degree whereby the secretions from the glands of the skin and mucous membranes become repellent to biting, sucking or chewing insects, e.g. mosquitoes, chiggers, ticks, etc., and that by maintaining a reduced dosage the repellent effect is continued.

Examples of materials which produce this result when ingested are flowers of sulfur (S); mixture of sulfur (S) and charcoal (C); mixture of sulfur (S) and cream of tartar; ($KHC_4H_4O_6$); edible sulfates; sulfides, except those of poisonous heavy metals, etc. The dosage is maintained below the limits at which sulfur produces a laxative or cathartic effect.

It has been found that a tablet of a mixture of 5 grains of sulfur or 5 plus 1 grain of $KHC_4H_4O_6$ taken three times daily over a period of several days produces the repellent effect and reducing the dosage to twice daily will maintain the repellent indefinitely.

The same is true of a tablet containing a mixture of sulfur (S) and carbon (C) and substantially the same dosage is effective.

When suppositories are used a soluble sulfate may be suspended in a vehicle such as glycerine of cocoa butter and the dosage would be as much as five times the concentration as that when ingested.

All dosages, however have to be related to the height, weight, and skin pigmentation and overall health of the subject.

The systemic metabolism of S in the human body is such that it appears in the saliva as sulfocyanates, e.g. KSCN, and in secretions from the cutaneous glands (sweat or perspiration) which by analyses contain among other substances, $K_2SO_4$, $Na_2SO_4$, $NH_4HSO_4$, $H_2S$ and $CH_3SH$.

By increasing the intake of elemental sulfur or sulfur compounds it appears that there is an increase in the sulfur products occuring in the excretions from the skin and mucous membranes and that by controlled dosage the level is increased to a degree whereby sucking, biting and chewing insects are repelled, but the cathartic actions of the sulfur products is avoided. It appears that the mixture of sulfur and cream of tartar is the preferred embodiment since cream of tartar has a mild diaphoretic effect. It also appears desirable that the compounds ingested should be metabolized by the human body to produce compounds in the sweat and saliva that have relatively high vapor pressures, such as hydrogen sulfide ($H_2S$) and methylthioalcohol ($CH_3SH$), at the body and air temperature at which the sucking and biting insects may be present.

Although the present invention has been described with preferred embodiments, it is to be understood that variations and modifications may be resorted to, without departing from the spirit and scope of this invention, as those skilled in the art will readily understand. Such modifications and variations are considered to be within the purview and scope of the appended claims.

What is claimed is:

1. A method of repelling chewing, sucking, and biting insects from the human body which comprises initially introducing into the body exposed to said insects an amount of sulfur, or sulfur mixed or combined with other substances and utilizing the metabolism in the body to produce sulfur compounds repellant to insects on the exposed surfaces of the body in sufficient concentration to repel said insects.

2. The method of claim 1 which comprises maintaining the concentration of sulfur compounds repellant to insects on the surfaces of the body by introducing reduced amounts of sulfur, or sulfur mixed or combined with other substances at regular less frequent intervals.

3. The method of claim 2 which comprises maintaining the concentration of sulfur by inserting a suppository containing 25 grains of sulfur in a mixture twice daily.

4. The method of claim 1 in which the sulfur is in the form of flowers of sulfur.

5. The method of claim 1 in which the sulfur mixture is sulfur mixed with charcoal.

6. The method of claim 1 in which the mixture is comprised of 5 grains of sulfur and 1 grain of cream of tartar ($KHC_4H_4O_6$).

7. The method of claim 1 in which the sulfur compound is an edible sulfate.

8. The method of claim 1 in which the sulfur compound is a sulfide exclusive of the sulfides of heavy poisonous metals.

9. The method of claim 1 in which the sulfur mixture or compound is introduced into the body by ingesting the said sulfur or sulfur mixture or compound.

10. The method of claim 1 in which the sulfur compound is a soluable sulfate dissolved or suspended in glycerine or cocoa butter.

11. The method of claim 10 in which the suspension or solution is introduced into the body by inserting a rectal suppository.

12. The method of claim 11 which comprises initially introducing the sulfur, sulfur mixture or compound in the body by inserting a suppository containing approximately 25 grains of sulfur in a mixture three times daily.

13. The method of claim 1 in which the sulfur is colloidal and carried in sterile water.

14. The method of claim 13 in which the colloidal sulfur and water are introduced into the body by injecting direcly into the body tissue.

15. The method of claim 1 which comprises initially introducing the sulfur, or sulfur mixture or compound into the body by ingesting tablets containing 5 grains of sulfur, free or in a compound or mixture three times daily.

16. The method of claim 2 which comprises maintaining the concentration of sulfur componds on the body surfaces by ingesting tablets containing 5 grains of sulfur free or in a compound or mixture twice daily.

* * * * *